(12) United States Patent
Teigelkamp et al.

(10) Patent No.: US 8,063,180 B2
(45) Date of Patent: *Nov. 22, 2011

(54) ANTIBODIES DIRECTED AGAINST PROTHROMBIN FRAGMENT F1+2, THE PREPARATION AND USE THEREOF

(75) Inventors: Stefan Teigelkamp, Niederwalgern (DE); Konrad Braun, Ebsdorfergrund (DE)

(73) Assignee: Seimens Healthcare Diagnostics Products GmbH, Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/591,303

(22) Filed: Nov. 16, 2009

(65) Prior Publication Data

US 2010/0158932 A1 Jun. 24, 2010

Related U.S. Application Data

(62) Division of application No. 10/992,351, filed on Nov. 19, 2004, now Pat. No. 7,795,403.

(30) Foreign Application Priority Data

Nov. 20, 2003 (DE) .................. 103 54 403

(51) Int. Cl.
*C07K 7/06* (2006.01)
(52) U.S. Cl. ..... 530/329; 435/7.1; 435/7.93; 424/139.1; 424/141.1; 424/145.1; 424/184.1; 530/387.9; 530/388.1; 530/388.25
(58) Field of Classification Search .................. None
See application file for complete search history.

(56) References Cited

U.S. PATENT DOCUMENTS

| | | | |
|---|---|---|---|
| 4,208,479 A * | 6/1980 | Zuk et al. | 435/7.9 |
| 5,071,954 A | 12/1991 | Pelzer et al. | |
| 6,541,275 B1 | 4/2003 | Ruiz et al. | |
| 2006/0189538 A1 * | 8/2006 | Secombes et al. | 514/15 |

FOREIGN PATENT DOCUMENTS

| | | |
|---|---|---|
| EP | 0303983 A2 | 2/1989 |
| EP | 0594576 B1 | 7/1999 |
| WO | WO 00/14209 A1 | 3/2000 |
| WO | WO 03/062271 A1 | 7/2003 |
| WO | WO 2004/111636 A2 | 12/2004 |

OTHER PUBLICATIONS

Janeway et al., Immunobiology, 3$^{rd}$ edition, 1997, Garland Publishing, pp. 2:6-2:8.*
Church et al., Modulation of Human Prothrombin Activation on Phospholipid Vesicles and Platelets Using Monoclonal Antibodies to Prothrombin Fragment 2, J. Biol. Chem. 266:8384-8391 (1991).
Kim et al., A Peptide Derived from Human Prothrombin Fragment 2 Inhibits Prothrombinase and Angiogenesis, Thrombosis Research 106:81-87 (2002).
Campbell A.M., Monoclonal Antibody Technology, Elsevier Science Publishers B.V., pp. 1-32 (1984).
Harlow et al., Antibodies: A Laboratory Manual, Cold Spring Harbor Laboratory, p. 76 (1988).
Bezeaud et al., Quantitation of Prothrombin Activation Products in Human Urine, British Journal of Haematology 58:597-606 (1984).

* cited by examiner

*Primary Examiner* — Michael Szperka
(74) *Attorney, Agent, or Firm* — Finnegan, Henderson, Farabow, Garrett & Dunner, L.L.P.

(57) ABSTRACT

The invention relates to antibodies directed against $F_{1+2}$, to the preparation and use thereof, especially in therapy and diagnosis. The antibodies bind to an epitope on the N-terminal half of the $F_2$ fragment of prothrombin.

20 Claims, No Drawings

ANTIBODIES DIRECTED AGAINST PROTHROMBIN FRAGMENT F1+2, THE PREPARATION AND USE THEREOF

This is a division of application Ser. No. 10/992,351, filed Nov. 19, 2004 now U.S. Pat. No. 7,795,403, and claims the benefit of priority of German Patent Application No. 10354403.8, filed Nov. 20, 2003, both of which are incorporated herein by reference in their entirety.

The invention relates to antibodies directed against prothrombin fragment $F_{1+2}$, and to the preparation and use thereof.

The conversion of prothrombin to active thrombin with formation of fragments represents a central event in the progression of the coagulation cascade. Immunochemical determination of prothrombin fragment $F_{1+2}$ makes quantification of the actually formed thrombin possible.

The significance of determining prothrombin fragment $F_{1+2}$ (called "$F_{1+2}$" hereinafter) lies in the diagnosis of hypercoagulability states and thrombotic events. Elevated levels are detected in patients with thromboses, pulmonary embolism, disseminated intravascular coagulation (DIC), polytrauma and sepsis. An increase in the $F_{1+2}$ concentration in the plasma of patients with hereditary protein C or protein S deficiency has likewise been described. During therapy with oral anticoagulants there is found to be a marked reduction in the $F_{1+2}$ level below the reference range.

The difficulty generally associated with $F_{1+2}$ assays is that prothrombin is present in large excess compared with $F_{1+2}$ in the sample, so that the anti-$F_{1+2}$ antibodies to be employed in the assay must distinguish very specifically between prothrombin fragments $F_2$ (called "$F_2$" hereinafter) released by cleavage, and $F_{1+2}$ on the one hand, and intact prothrombin on the other hand. The preparation of such specific antibodies is described in EP-0 303 983. A commercially available enzyme immunoassay for determining the concentration of prothrombin fragment $F_{1+2}$ makes use for example of polyclonal rabbit anti-$F_{1+2}$ antibodies prepared in this way. It is important for the specificity of anti-$F_{1+2}$ antibodies that they bind to an epitope which comprises at least the four carboxy-terminal amino acids of the $F_2$ and $F_{1+2}$ fragments (Ile-Glu-Gly-Arg-OH; SEQ ID NO:1). Although corresponding monoclonal anti-$F_{1+2}$ antibodies have also been known for some years (U.S. Pat. No. 6,541,275, EP-0 594 576), and the general advantages of monoclonal antibodies are also undisputed among skilled workers, they have not to date been employed in commercial $F_{1+2}$ assays. Since ordinarily sandwich immunoassays are employed to determine the $F_{1+2}$ concentration, two anti-$F_{1+2}$ antibodies are required. It has evidently not been possible to date to find a combination, in particular of monoclonal antibodies, which permits $F_{1+2}$ determination with high sensitivity and specificity.

The present invention was accordingly based on the object of providing an assay for determining prothrombin fragment $F_{1+2}$ with increased precision, reproducibility and improved discrimination of pathological and non-pathological samples.

This object is achieved by provision of the methods and aspects of the invention described in the claims.

In particular, the object is achieved by providing monoclonal antibodies against prothrombin fragment $F_{1+2}$ which bind to an epitope on the N-terminal half of the $F_2$ fragment of prothrombin (called "secondary antibodies" hereinafter). In combination with antibodies whose epitopes include the four carboxy-terminal amino acids of the $F_2$ and $F_{1+2}$ fragments (called "primary antibodies" hereinafter), these secondary antibodies form the basis for an improved sandwich immunoassay for $F_{1+2}$ determination.

It has surprisingly emerged from an immunization study that although all the tested primary antibodies showed binding to $F_{1+2}$, only four of 38 tested secondary antibodies bind specifically to $F_{1+2}$. Although 75% of the tested primary antibodies were suitable for constructing a sandwich immunoassay, only one of the remaining four secondary antibodies was. This low yield indicates that the secondary antibody must have particular properties. The epitope recognized by the secondary antibody is particularly important in this connection. The epitope for an antibody of the invention has been unambiguously identified as a peptide having the amino acid sequence Ser-Pro-Pro-Leu-Glu-Gln-Cys (amino acids 9 to 15 of SEQ ID NO:2).

Specific embodiments of the invention are explained in detail below:

One aspect of this invention are peptides consisting of 5-25 amino acids, preferably of 5 to 21 amino acids, very particularly preferably of 5-12 amino acids, which comprise the amino acid sequence Pro-Leu-Glu-Gln-Cys (amino acids 11 to 15 of SEQ ID NO:2). Preferred peptides of the invention are those having the amino acid sequence Ser-Glu-Gly-Ser-Ser-Val-Asn-Leu-Ser-Pro-Pro-Leu -Glu-Gln-Cys-Val-Pro-Asp-Arg-Gly-Gln-Gln-Tyr-Gln-Gly (amino acids 1 to 25 of SEQ ID NO:2) or a fragment thereof, in particular a peptide having amino acid sequence Ser-Pro-Pro-Leu-Glu-Gln-Cys (amino acids 9 to 15 of SEQ ID NO:2).

The term "peptide" for the purposes of this invention includes amides which decompose on hydrolysis into amino acids, for example amino acid polymers such as, for example, polypeptides, oligopeptides, proteins or protein fragments.

The peptides of the invention can be used as immunizing antigen for preparing the antibodies of the invention or else for the affinity chromatography purification of the antibodies of the invention. The peptides of the invention can also be used in a method for the quantitative or qualitative detection of an analyte, preferably $F_{1+2}$. The peptides of the invention can also be associated with a solid phase and/or a component of a signal-generating system.

A further preferred aspect of the invention are antibodies which bind to an epitope on the N-terminal half of the $F_2$ fragment of prothrombin, i.e. antibodies which bind to Ser-Glu-Gly-Ser-Ser-Val-Asn-Leu-Ser-Pro-Pro-Leu-Glu-Gln-Cys-Val -Pro-Asp-Arg-Gly-Gln-Gln-Tyr-Gln-Gly-Arg-Leu-Ala-Val-Thr-Thr-His -Gly-Leu-Pro-Cys-Leu-Ala-Trp-Ala-Ser-Ala-Gln-Ala-Lys-Ala-Leu-Ser -Lys-His-Gln-Asp-Phe-Asn-Ser-Ala-Val-Gln-Leu-Val-Glu-Asn (SEQ ID NO:2).

The term "antibody" means for the purposes of this invention an immunoglobulin, e.g. an immunoglobulin of the class or subclass IgA, IgD, IgE, $IgG_1$, $IgG_{2a}$, $IgG_{2b}$, $IgG_3$, $IgG_4$, IgM. An antibody has at least one binding site (frequently called paratope) for an epitope (frequently also called antigenic determinant) on an antigen or hapten. Such an epitope is characterized for example by its three-dimensional structure and/or by the presence of polar and/or nonpolar groups. The binding site of the antibody is complementary to the epitope. The antigen-antibody reaction or the hapten-antibody reaction functions by the so-called "lock and key principle", and is usually highly specific, i.e. the antibodies are able to distinguish small differences in the primary structure, in the charge, in the spatial configuration and the steric arrangement of the antigen or hapten. In particular, the so-called complementarity determining regions of the antibody contribute to the binding of the antibody to the antigen or hapten.

The term "antigens" includes monovalent and polyvalent antigens. A polyvalent antigen is a molecule or a molecule complex to which simultaneous binding of more than one immunoglobulin is possible, whereas a monovalent antigen can bind only a single antibody at each particular time. Hapten is normally the designation given to a molecule which is not immunogenic per se but which is normally bound to a carrier for immunization purposes.

The term antibody means for the purposes of this invention not only complete antibodies but expressly also antibody fragments such as, for example, Fab, Fv, F(ab')$_2$, Fab'; and also chimeric, humanized, bi- or oligospecific, or single-chain antibodies; in addition aggregates, polymers and conjugates of immunoglobulins and/or fragments thereof, as long as the properties of binding to the antigen or hapten are retained. Antibody fragments can be prepared for example by enzymatic cleavage of antibodies with enzymes such as pepsin or papain. Antibody aggregates, polymers and conjugates can be generated by diverse methods, e.g. by thermal treatment, reaction with substances such as glutaraldehyde, reaction with immunoglobulin-binding molecules, biotinylation of antibodies and subsequent reaction with streptavidin or avidin, etc.

An antibody for the purposes of this invention may be a monoclonal or a polyclonal antibody. The antibody can have been prepared by conventional methods, e.g. by immunization of a human or of an animal, such as, for example, mouse, rat, guinea pig, rabbit, horse, sheep, goat, chicken (see also Messerschmid (1996) BIOforum, 11:500-502), and subsequent isolation of the antiserum; or by establishing hybridoma cells and subsequent purification of the secreted antibodies; or by cloning and expression of the nucleotide sequences, or modified versions thereof, which encode the amino acid sequences which are responsible for the binding of the natural antibody to the antigen and/or hapten.

Antibodies of the invention are in particular those antibodies which bind to a peptide consisting of 5-25 amino acids, preferably of 5 to 21 amino acids, very particularly preferably of 5-12 amino acids, which includes the amino acid sequence Pro-Leu-Glu-Gln-Cys (amino acids 11 to 15 of SEQ ID NO:2). Very preferred antibodies for the purposes of this invention are antibodies which bind specifically to the peptide having the amino acid sequence Ser-Glu-Gly-Ser-Ser-Val-Asn-Leu -Ser-Pro-Pro-Leu-Glu-Gln-Cys-Val-Pro-Asp-Arg-Gly-Gln-Gln-Tyr-Gln-Gly (amino acids 1 to 25 of SEQ ID NO:2) or to a fragment of this peptide, in particular to a peptide having the amino acid sequence Ser-Pro-Pro-Leu-Glu-Gln-Cys (amino acids 9 to 15 of SEQ ID NO:2).

Particularly preferred antibodies for the purposes of this invention are also the antibodies produced by the hybridoma cell line 92-195/097. This hybridoma cell line was deposited on Aug. 15, 2003, at the DSMZ-Deutsche Sammlung von Mikroorganismen and Zellkulturen GmbH, Mascheroder Weg 1b, 38124 Brunswick, Germany, under accession number DSM ACC2607.

A further aspect of this invention are specific binding partners which bind to an epitope which is recognized by an antibody of the invention.

A "specific binding partner" means a member of a specific binding pair. The members of a specific binding pair comprise two molecules each of which have at least one structure complementary to a structure of the other molecule, the two molecules being able to bind through a binding of the complementary structures. The term molecule also includes molecule complexes such as, for example, enzymes consisting of Apo enzyme and coenzyme, proteins consisting of a plurality of subunits, lipoproteins consisting of protein and lipids, etc. Specific binding partners may be substances which occur naturally or else have been prepared for example by chemical synthesis, microbiological techniques and/or methods of genetic manipulation. Examples to be mentioned to illustrate the term specific binding partners, but not to be understood as restrictive, are: thyroxine-binding globulin, steroid-binding proteins, antibodies, antigens, haptens, enzymes, lectins, nucleic acids, repressors, oligo- and polynucleotides, protein A, protein G, avidin, streptavidin, biotin, complement component C1q, nucleic acid-binding proteins, etc. Specific binding pairs are, for example: antibody-antigen, antibody-hapten, operator-repressor, nuclease-nucleotide, biotin-avidin, lectin-polysaccharide, steroid-steroid-binding protein, drug-drug receptor, hormone-hormone receptor, enzyme-substrate, IgG-protein A, complementary oligo- or polynucleotides, etc.

The provision of the antibodies of the invention now makes it possible for the skilled worker to identify, e.g. by competition experiments (see also Peters et al. (1985) Monoklonale Antikörper, Springer Verlag, chapter 12.2 "Epitop-Analyse"), other specific binding partners, antibodies expressly included, which bind to the epitope of an antibody of the invention. It is thus now possible by techniques known to the skilled worker to select specific binding partners with the aid of phage display libraries, via synthetic peptide databases or by means of recombinatorial antibody libraries (Larrick & Fry (1991) Human Antibodies and Hybridomas, 2:172-189).

This invention also relates to an antibody of the invention which is associated with a solid phase and/or a component of a signal-generating system.

The term "solid phase" for the purposes of this invention comprises an article which consists of porous and/or nonporous, usually water-insoluble material, and which may have a wide variety of shapes, such as, for example, vessel, tube, microtiter plate, bead, microparticle, rod, strip, filter paper or chromatography paper, etc. The surface of the solid phase is usually hydrophilic or can be made hydrophilic. The solid phase may consist of a wide variety of materials such as, for example, of inorganic and/or of organic materials, of synthetic, of naturally occurring and/or of modified naturally occurring materials. Examples of solid phase materials are polymers such as, for example, cellulose, nitrocellulose, cellulose acetate, polyvinyl chloride, polyacrylamide, crosslinked dextran molecules, agarose, polystyrene, polyethylene, polypropylene, polymethacrylate or nylon; ceramic; glass; metals, especially noble metals such as gold and silver; magnetite; mixtures or combinations thereof; etc. The term solid phase also encompasses cells, liposomes or phospholipid vesicles.

The solid phase may have a coating composed of one or more layers, e.g. of proteins, carbohydrates, lipophilic substances, biopolymers, organic polymers or mixtures thereof, in order for example to diminish or prevent nonspecific binding of constituents of the sample to the solid phase, or in order for example to achieve improvements in relation to the suspension stability of particulate solid phases, the storage stability, the shaping stability or the resistance to UV light, microbes or other agents having a damaging effect.

A "signal-generating system" may comprise one or more components, where at least one component comprises a detectable label. A label means any molecule which can itself produce a signal or can induce the production of a signal such as, for example, a fluorescent substance, a radioactive substance, an enzyme, or a chemiluminescent substance. The signal can be detected or measured for example on the basis of the enzymic activity, the luminescence, the light absorption, the light scattering, the emitted electromagnetic or radioactive radiation, or a chemical reaction.

A label is able itself to generate a detectable signal, so that no further components are necessary. Many organic molecules absorb ultraviolet and visible light, and the energy transferred by the absorption of light can put these molecules into an excited energy state, and they emit the absorbed energy in the form of light of a different wavelength from that of the incident light. Other labels in turn are able to generate directly a detectable signal, such as, for example, radioactive isotopes or dyes.

Other labels in turn require further components to generate the signal, i.e. the signal-producing system includes in such a case all the components required for signal generation, such as, for example, substrates, coenzymes, quenchers, accelerators, additional enzymes, substances which react with enzyme products, catalysts, activators, cofactors, inhibitors, ions, etc.

Suitable labels (see also EP-A2-0 515 194; U.S. Pat. No. 5,340,716; U.S. Pat. No. 5,545,834; Bailey et al. (1987) J. Pharmaceutical & Biomedical Analysis 5:649-658) are, for example, enzymes including horseradish peroxidase, alkaline phosphatase, glucose-6-phosphate dehydrogenase, alcohol dehydrogenase, glucose oxidase, β-galactosidase, luciferase, urease and acetylcholinesterase; dyes; fluorescent substances including fluorescein isothiocyanate, rhodamine, phycoerythrin, phycocyanin, ethidium bromide, 5-dimethylamino-naphthalene-1-sulfonyl chloride and fluorescent chelates of rare earths; chemiluminescent substances including luminol, isoluminol, acridinium compounds, olefin, enol ether, enamine, aryl vinyl ether, dioxene, arylimidazole, lucigenin, luciferin and aequorin; sensitizers including eosin, 9,10-dibromoanthracene, methylene blue, prophyrin, phthalocyanin, chlorophyll, Rose Bengal; coenzymes; enzyme substrates; radioactive isotopes including $^{125}I$ $^{131}I$, $^{14}C$, $^{3}H$, $^{32}P$, $^{35}S$, $^{14}C$, $^{51}Cr$, $^{59}Fe$, $^{57}Co$ and $^{75}Se$; particles including magnetic particles or particles, preferably latex particles, which themselves may be labeled for example with dyes, sensitizers, fluorescent substances, chemiluminescent substances, isotopes or other detectable labels; sol particles including gold or silver sols; liposomes or cells which may themselves be labeled with detectable labels; etc.

A signal-generating system may also include components which are able to engage in a detectable interaction when spatially close to one another, e.g. in the form of energy donors and energy recipients such as, for example, photosensitizers and chemiluminescent substances (EP-A2-0 515 194), photosensitizers and fluorophores (WO 95/06877), radioactive iodine-125 and fluorophores (Udenfriend et al. (1985) Proc. Natl. Acad. Sci. 82:8672-8676), fluorophores and fluorophores (Mathis (1993) Clin. Chem. 39:1953-1959) or fluorophores and fluorescence quenchers (U.S. Pat. No. 3,996,345).

An interaction between the components includes direct transfer of energy between the components, e.g. by emission of light or electrons, and via short-lived reactive chemical molecules. Also included thereby are processes in which the activity of one component is inhibited or enhanced by one or more others, for example inhibiting or increasing enzymic activity or inhibiting, increasing or altering (e.g. wavelength shift, polarization) the electromagnetic radiation emitted by the influenced component. The interaction between the components also includes enzyme cascades. In this case, the components are enzymes, at least one of which provides the substrate for another, so that a maximum or minimum reaction rate of the coupled substrate conversion results.

An efficient interaction between the components usually takes place when they are spatially adjacent, i.e. for example within a range of distance of a few μm, in particular within a range of distance of below 600 nm, preferably below 400 nm, very particularly preferably of below 200 nm.

Microparticles are frequently used as solid phase and/or as label. The term "microparticles" means for the purposes of this invention particles which have an approximate diameter of not less than 20 nm and not more than 20 μm, normally between 40 nm and 10 μm, preferably between 0.1 and 10 μm, particularly preferably between 0.1 and 5 μm, very particularly preferably between 0.15 and 2 μm. The microparticles may have regular or irregular shapes. They may be spheres, spheroids, spheres with larger or smaller cavities or pores. The microparticles may consist of organic or inorganic material or of a mixture or combination of the two. They may also consist of a porous or nonporous, a swellable or nonswellable material. The microparticles can in principle have any density, but particles having a density close to the density of water, such as about 0.7 to about 1.5 g/ml, are preferred. The preferred microparticles can be suspended in aqueous solutions and are maximally stable in suspension. They may be transparent, partially transparent or opaque. The microparticles may consist of a plurality of layers such as, for example, the so-called core-and-shell particles having a core and one or more enveloping layers. The term microparticle includes for example dye crystals, metal sols, silica particles, glass particles, magnetic particles, polymer particles, oil drops, lipid particles, dextran, and protein aggregates. Preferred microparticles are particles which can be suspended in aqueous solutions and consist of water-insoluble polymer material, in particular of substituted polyethylenes. Latex particles are very particularly preferred, for example composed of polystyrene, acrylic acid polymers, methacrylic acid polymers, acrylonitrile polymers, acrylonitrile-butadiene-styrene, polyvinyl acetate-acrylate, polyvinylpyridine, vinyl chloride-acrylate. Latex particles having reactive groups on their surface such as, for example, carboxyl, amino or aldehyde groups allowing covalent linkage for example of specific binding partners to the latex particles are of particular interest. The preparation of latex particles is described for example in EP 0 080 614, EP 0 227 054 and EP 0 246 446.

The term "associated" has a wide meaning and includes, for example, covalent and noncovalent linkage, direct and indirect linkage, adsorption onto a surface and entrapment in a recess or a cavity, etc. In the case of a covalent linkage, the antibodies or binding partners are linked via a chemical bond to the solid phase or to the label. Examples of a noncovalent linkage are surface adsorption, entrapment in cavities or linkage of two specific binding partners. Besides direct linkage to the solid phase or the label, it is possible for the antibodies or binding partners also to be linked indirectly to the solid phase or the label via specific interaction with other specific binding partners (see also EP-A2-0 411 945). This is to be illustrated in detail by means of examples: the biotinylated antibody can be linked to the label via label-bound avidin; or a fluorescein-antibody conjugate can be linked to the solid phase via solid phase-bound anti-fluorescein antibodies; or the antibody can be linked to the solid phase or the label via immunoglobulin-binding proteins.

A further aspect of this invention are antibodies of the invention or specific binding partners which are used as an in vitro diagnostic aid or as a constituent of an in vitro diagnostic aid.

In an in vitro diagnostic aid, the analyte to be detected, e.g. $F_{1+2}$, is detected in a sample outside a living human or animal body, or the concentration or amount thereof is determined.

A "sample" means for the purposes of the invention the material which presumably contains the substance to be detected (for examples of the term "analyte", see EP-A2-0 515 194, pages 8-15). The term sample includes for example biological liquids or tissues, in particular from humans and animals, such as blood, plasma, serum, sputum, exudate, bronchoalveolar lavage, lymph, synovial fluid, seminal fluid, vaginal mucus, feces, urine, CSF, hair, skin, tissue samples or sections. Also included are cell culture samples, plant fluids or tissues, forensic samples, water and sewage samples, foodstuffs, medicaments. It is necessary where appropriate for the samples to be pretreated in order to make the analytes amenable to the detection method or in order to remove interfering constituents of the sample. Such pretreatment of samples may include removal and/or lysis of cells, precipitation, hydrolysis or denaturation of constituents of the sample such as, for example, proteins, centrifugation of samples, treatment of the sample with organic solvents such as, for example, alcohols, especially methanol; treatment of the sample with detergents. The sample is frequently transferred into a different, usually aqueous, medium which should interfere as little as possible with the detection method.

The antibodies of the invention can be used in a method for the quantitative or qualitative detection of an analyte, preferably $F_2$ and/or $F_{1+2}$ and/or prothrombin in a sample.

In a quantitative detection, the amount, the concentration or the activity (e.g. enzymic activity) of the analyte in the sample is measured. The term "quantitative detection" also includes semiquantitative methods which only estimate the approximate amount, concentration or activity of the analyte in the sample or can serve only to indicate a relative amount, concentration or activity. A qualitative detection means merely detection of the presence of the analyte in the sample or indication that the concentration or activity of the analyte in the sample is below or above a particular or a plurality of particular threshold values.

The invention thus also relates to methods for the quantitative or qualitative detection of an analyte, preferably $F_2$ and/or $F_{1+2}$, in a sample and suitable reagents therefor.

Analytes are frequently detected by employing binding assays in which the presence, absence or amount of the analyte in a sample can be concluded from a specific binding of analyte to be detected to analyte-specific binding partners. Immunoassays or else methods in which oligo- or polynucleotides are hybridized are examples of binding assays.

So-called "heterogeneous binding assays" are characterized by one or more separation steps and/or washing steps. The separation can take place for example by immunoprecipitation, precipitation with substances such as polyethylene glycol or ammonium sulfate, filtration, magnetic removal, attachment to a solid phase. Such a "solid phase" consists of porous and/or nonporous, usually water-insoluble material. It may have a wide variety of shapes, such as, for example: vessel, tube, microtiter plate, bead, microparticle, rod, strip, filter paper or chromatography paper, etc. In heterogeneous binding assays in sandwich format, usually one of the analyte-specific binding partners is linked to a solid phase and serves to remove the "analyte/analyte-specific binding partner" binding complex from the liquid phase, while the other analyte-specific binding partner carries a detectable label (e.g. an enzyme, a fluorescent or chemiluminescent label, etc.) for detecting the binding complex. These assay methods are divided further into so-called one-step sandwich assays in which the two specific binding partners are incubated simultaneously with the sample, and into two-step sandwich assays in which the sample is incubated firstly with the solid phase reagent and, after a separation and washing step, the solid phase-bound binding complex of analyte and analyte-specific binding partner is incubated with the detection reagent.

In "homogeneous binding assays" there is no separation between components of the signal-generating system which are free and those bound to the "analyte/analyte-specific binding partner" complex. The assay mixture, which contains the analyte-specific binding partners, the signal-generating components and the sample, is measured after or even during the binding reaction, without a further separation and/or washing step, and the corresponding measured signal is determined. Examples of homogeneous immunoassays (see also Boguslaski & Li (1982) Applied Biochemistry and Biotechnology, 7:401-414) are many turbidimetric and nephelometric methods, where the analyte-specific binding partners used for detection can be associated with latex particles; EMIT® assays; CEDIA® assays; fluorescence polarization immunoassays; luminescent oxygen channeling immunoassays ("LOCI", see EP-A2-0 515 194; Ullman et al. (1994) Proc. Natl. Acad. Sci., 91:5426-5430; Ullman et al. (1996) Clinical Chemistry, 42:1518-1526); etc. In a homogeneous sandwich immunoassay, such as, for example, a nephelometric latex assay, the antibody reagents are incubated together with the sample, and the signal is measured during and/or after the incubation, without carrying out a separation or washing step before the measurement. In other words: there is no separation of antibody-bound analyte from free analyte or from antibodies which have bound no analyte.

Homogeneous and heterogeneous binding assays can also be carried out in the form of a so-called "sandwich assay". In this case, the analyte is, for example, in a heterogeneous binding assay, bound by a solid phase-associated analyte-specific binding partner and by an analyte-specific binding partner which is associated with a component of a signal-generating system. The analyte-specific binding partners in sandwich immunoassays can be formed by antibodies or antigens or haptens.

A further specific embodiment of a heterogeneous or homogeneous binding assay is the "indirect immunoassay". The analyte is in this case an antibody. One of the analyte-specific binding partners is the antigen or a modified antigen of the antibody to be detected (=analyte) and the other analyte-specific binding partner is usually an immunoglobulin-binding protein such as, for example, an antibody which is able to bind specifically the antibody to be detected (=analyte).

In a homogeneous or heterogeneous "competitive binding assay", sample analyte and reagent analyte (for example a "modified analyte" such as, for example, a labeled or tagged analyte, analyte fragment or analyte analog) compete for binding to a limited number of analyte-specific binding partners. Examples to illustrate the principle: (i) sample analyte competes with reagent analyte which is associated with a component of a signal-generating system for binding to solid phase-associated analyte-specific binding partners or (ii) sample analyte competes with solid phase-associated analyte (=reagent analyte) for binding to analyte-specific binding partners which are associated with a component of a signal-generating system.

It is also possible to detect $F_{1+2}$ with the antibodies of the invention for example by methods such as, for example: Western blotting, dot blotting, immunoelectrophoresis, immunofixation electrophoresis, electroimmunodiffusion, immunoprecipitation, radial immunodiffusion, immunofixation, immunochromatography, latex agglutination, turbidimetric or nephelometric assay, homogeneous or heterogeneous binding assay, one- or two-step assay, sandwich assay, indirect assay, competitive assay, point-of-care tests, etc. These and other detection methods are described for example in "Labor and Diagnose", ed. L. Thomas, TH-Books Verlagsgesellschaft mbH, Frankfurt, 1998, chapter 60, or in "Laboratory Techniques in Biochemistry and Molecular Biology—

An Introduction to Radioimmunoassay and Related Techniques", ed. T. Chard, Elsevier, Amsterdam, 1987.

The term "point-of-care tests" or "POC tests" includes tests in which no separate analytical or measurement apparatus is required to carry out the test or evaluate the test. POC tests are based in many cases on immunochromatographic methods, immune complex removal by filtration and/or immunofixation techniques. POC tests are intended in particular for measurements on the spot, e.g. at the hospital bed or at home, for the emergency physician and/or the primary-care physician and less for the large laboratory. POC tests can in particular also be carried out by people having no detailed medical-technical training and experience in the area of laboratory medicine. The term "POC tests" also means for the purposes of this invention so-called home tests or OTC tests which may be carried out by medical laypeople, for example the various pregnancy tests marketed for home use. Other POC tests relate for example to detection of markers of myocardial infarction, drugs, medicaments, markers of infection and inflammation. In many POC tests, specific binding partners are, or become during the carrying out of the test, associated with or on filter or chromatography strips or disks. A positive or negative detection reaction can be linked for example to the appearance or nonappearance of a colored band in a particular test field, and/or the appearance or non-appearance of a particular symbol, e.g. a "+", a "−" and/or the intensity of the particular measured signal.

A POC test for $F_{1+2}$ can be designed for example as follows: sample and labeled antibodies able to bind to $F_{1+2}$ (preferably secondary antibodies) are applied to a test strip. Examples of suitable labels are colored latex particles, colloidal gold, enzymes, etc. If $F_{1+2}$ is present in the sample there will be formation of $F_{1+2}$/antibody complexes. These complexes migrate, for example by capillary force, towards a zone in which antibodies able to bind to other $F_{1+2}$ epitopes (preferably primary antibodies) are immobilized, or become immobilized during the test method (e.g. via a biotin-avidin bridge), e.g. in the form of a band. The labeled $F_{1+2}$/antibody complexes are bound in this zone and form a sandwich complex with the immobilized antibodies. The intensity of the label signal is in this case proportional to the $F_{1+2}$ sample concentration. In a competitive POC test method, for example $F_{1+2}$ and/or $F_{1+2}$ fragments can be immobilized, or become immobilized during the test method, in a zone of the test strip. This immobilized $F_{1+2}$ would compete with $F_{1+2}$ from the sample for binding to labeled anti-$F_{1+2}$ antibodies. An alternative possibility is also to employ immobilized anti-$F_{1+2}$ antibodies and labeled $F_{1+2}$ to design a competitive $F_{1+2}$ test.

A particularly preferred embodiment of the method of the invention is a nephelometric or turbidimetric assay, in particular an assay of this type in which antibodies of the invention—preferably associated with microparticles (in particular latex particles)—are employed.

Another aspect of the invention is a test kit which comprises one or more of the antibodies and/or peptides of the invention. Such a kit normally comprises all or only some components of a test in packaged form. The antibodies and/or peptides of the invention may be associated for example with one or more solid phases and/or one or more components of a signal-generating system. The test kit may comprise for example standards; controls; and other reagents such as, for example, buffers, washing solutions, measured signal-inducing solutions and/or enzyme substrate; cuvettes; pipettes and/or test instructions. A particularly preferred test kit of the invention comprises antibodies of the invention and/or peptides of the invention associated on latex particles.

The antibodies and peptides of the invention can also be used for affinity chromatography. The term "affinity chromatography" means a method for purifying and isolating substances, in particular biopolymers, which is based on the fact that many substances are able to enter into a selective, non-covalent, reversible binding with binding partners which are specific for them. The principle of the method is that the specific binding partner is linked, usually covalently, to an insoluble matrix (e.g. porous glasses, gels based on agarose, cellulose, dextran, polymer and silica gel) and brought into contact with a sample containing the substance. The substance which is sought is immobilized and retained because of its specific interaction with the matrix-linked specific binding partner, whereas all the other substances contained in the sample are removed by elution. Subsequently, the substance which is sought is detached from the matrix using a suitable eluent which abolishes the noncovalent binding between substance and specific binding partner (see also E. Buddecke (1989) Grundrisse der Biochemie, Walter de Gruyter, chapter 7 "Proteine").

Another aspect of this invention includes antibodies of the invention or peptides of the invention in a pharmaceutically acceptable, sterile injection medium. A pharmaceutically acceptable, sterile injection medium means for example a sterile, pyrogen-free solution, e.g. saline or another electrolyte solution, as is normally used for intravenous, intramuscular, intraperitoneal or subcutaneous administration of medicaments, vaccines or contrast agents.

Another aspect of this invention is in turn the use of the antibodies of the invention as diagnostic aid or as constituent of a diagnostic aid.

Another aspect of this invention is a method for preparing an antibody of the invention, which comprises employing for the immunization one or more peptides consisting of 5-25 amino acids, preferably of 5 to 21 amino acids, very particularly preferably of 5-12 amino acids, which comprise the amino acid sequence Pro-Leu-Glu-Gln-Cys (amino acids 11 to 15 of SEQ ID NO:2). The peptides particularly preferably employed as immunizing antigen in this method of the invention have the amino acid sequence Ser-Glu-Gly-Ser-Ser-Val-Asn-Leu-Ser-Pro-Pro -Leu-Glu-Gln-Cys-Val-Pro-Asp-Arg-Gly-Gln-Gln-Tyr-Gln-Gly (amino acids 1 to 25 of SEQ ID NO:2) or fragments thereof, with preference for the peptide having the amino acid sequence Ser-Pro-Pro-Leu-Glu-Gln-Cys (amino acids 9 to 15 of SEQ ID NO:2).

The antibodies of the invention can also be prepared by using naturally occurring and/or recombinant $F_{1+2}$, $F_2$ or prothrombin as immunizing antigen.

The peptides used as immunizing antigen may be unbound and/or carrier-bound when used for the immunization. Examples of typical carriers are proteins such as, for example, ovalbumin, albumin or hemocyanin, or polymers such as, for example, polyethylene glycol, poly-acrylamide or poly-d-glutamine-d-lysine. The peptides can be linked to these carriers for example with the aid of carbodiimide or glutaraldehyde, or else by means of a bifunctional reagent which may also act as spacer (for examples and coupling methods, see, for example, Wong S. (1993) Chemistry of Protein Conjugation and Cross-Linking, CRC Press, Inc, Boca Raton).

The immunizing antigen may be taken up for example in phosphate-buffered saline and be mixed with Freund's adjuvant. This emulsion can then be administered for example intradermally, intraperitoneally and/or subcutaneously to an animal, for example a rabbit, a mouse, a rat, a guinea pig, a horse, a sheep, a goat, a chicken, etc. Booster injections, for which the immunizing antigen can also be emulsified with incomplete Freund's adjuvant, may help to increase the immune response.

Polyclonal antibodies of the invention can be obtained from the antiserum of the immunized animals and can be further purified by affinity chromatography on a matrix to which for example $F_{1+2}$ or the peptides employed as immunizing antigen have been linked.

Monoclonal antibodies of the invention are generated by fusing, by generally known methods (see, for example, Harlow & Lane (1988) Antibodies: A Laboratory Manual, Cold Spring Harbor Laboratory, Cold Spring Harbor; Peters et al. (1985) Monoklonale Antikörper: Herstellung and Charakterisierung, Springer Verlag) the immune cells of immunized animals, such as, for example, of a mouse, with myeloma cells to generate monoclonal antibody-producing hybridoma cells, and subsequently isolating suitable clones. Selection of the clones producing the desired monoclonal antibodies is carried out with the aid of specific screening methods. These entail the binding specificity of the antibodies released into the cell culture supernatant, e.g. for the immunizing antigen, for any carrier of the immunizing antigen, for $F_{1+2}$, for prothrombin, being checked for example by means of an enzyme immunoassay, radioimmunoassay and/or Western blot. Hybridomas which produce antibodies of the invention are cloned. The hybridoma cell lines obtained in this way are then available for permanent production of monoclonal antibodies. Larger amounts of antibodies can be obtained for example from cell culture supernatant, in particular from fermentors or roller cultures, and from ascites.

Depending on the desired purpose of use, it is advantageous to employ only parts of the antibodies, such as, for example, Fab, F(ab')$_2$ or Fab' fragments. These can be generated for example by enzymatic cleavage methods known to the skilled worker (see also, for example, Harlow & Lane (1988) Antibodies: A Laboratory Manual, Cold Spring Harbor Laboratory, Cold Spring Harbor).

The antigen-binding sites of an antibody are located in the so-called variable domains which are encoded by the V genes. The known genetic engineering methods (see, for example, Sambrook et al. (1989) Molecular Cloning: A Laboratory Manual, Cold Spring Harbor Laboratory, Cold Spring Harbor, 2nd edition; McCafferty et al. (1990) Nature 348:552-554) can be used also to find the corresponding nucleic acid sequence of an antibody of the invention, and thus also the corresponding amino acid sequence, where this was not previously known from amino acid sequencing. Starting material which can be employed for such analyses is the hybridoma cells or the antibody-producing immune cells of immunized animals.

It is possible with knowledge of the nucleic and/or amino acid sequence and with the aid of conventional methods of genetic manipulation and molecular biology (see also Johnson & Chiswell (1993) Current Opinion in Structural Biology, 3:564-571) then to prepare humanized, chimeric, bi- or oligospecific antibodies, and peptides derived from the complementarity-determining region (minimal recognition units), single-chain fragments, and/or functional fusion products, e.g. recombinantly prepared antibody-enzyme constructs (see, for example, Larrick & Fry (1991) Human Antibodies and Hybridomas, 2:172-189; Kitano et al (1986) Appl. Microbiol. Biotechnol, 24:282-286; Thompson et al. (1986) J. Immunol. Methods, 94:7-12) which bind to an epitope on the N-terminal half of the $F_2$ fragment of prothrombin, in particular to a peptide of the invention. It is possible with such peptides included by the term "antibodies" for example to reduce the immunogenicity and/or enhance the efficacy on administration as medicament or in vivo diagnostic aid, and/or advantages for use as or in an in vitro diagnostic aid emerge. The antibodies can also be prepared where appropriate with the aid of methods of genetic manipulation in plant— such as, for example, yeast cells—(Fischer et al. (1999) Biol. Chem., 380:825-839; Hiatt et al. (1992) Genetic Engineering, 14:49-64), animal and prokaryotic cells (see, for example, WO 95/25172), and isolated human cells.

A further aspect of this invention are also animal, plant or prokaryotic cells, and isolated human cells, which produce an antibody of the invention. A preferred embodiment of this invention includes hybridoma cell lines which produce the antibodies of the invention, for example the hybridoma cell line 92-195/097. This hybridoma cell line was deposited at the DSMZ Deutsche Sammlung von Mikroorganismen and Zellkulturen GmbH, Mascheroder Weg 1b, 38124 Brunswick, Germany, with the accession number DSM ACC2607.

The examples described below serve to throw light on examples of individual aspects of this invention and are not to be understood as restrictive.

EXAMPLES

Example 1

Prothrombin Purification

Commercially available prothrombin preparations can be employed as starting material for preparing the immunizing antigen. If the purity of these products is inadequate, the prothrombin should be isolated by chromatography before it is employed for the immunization. Chromatographic purification of prothrombin may appear for example as follows:

1. Fractionation on an anion exchanger (MonoQ-Sepharose) in citrate buffer (25 mM, pH 6) and use of the fractions which show prothrombin activity. This step reduces the concentration of factor X. Elution with 1 M NaCl.

2. Fractionation on heparin-Sepharose in citrate buffer (25 mM, pH 6) and use of the fractions which show prothrombin activity. This step further reduces the concentration of factor X. Elution with 1 M NaCl.

3. Removal of protein C by affinity chromatography in citrate buffer (25 mM, pH 6) with a monoclonal antibody against protein C. The prothrombin-containing flow-through is used further.

4. Changing the buffer to 50 mM citrate/150 mM NaCl, pH 6, by gel chromatography on Sephadex G200.

5. Removal of remaining factor X by affinity purification in a batch method in citrate buffer (25 mM, pH 6) with a monoclonal antibody against factor X. The prothrombin-containing supernatant is used for the immunization.

Example 2

Preparation of Monoclonal Antibodies

A) Monoclonal Primary Antibodies

The monoclonal primary antibody can be prepared by the methods described in EP-0303983 and U.S. Pat. No. 6,541,275.

B) Monoclonal Secondary Antibodies

The secondary antibodies were prepared by using purified prothrombin (see example 1) as immunizing antigen (20 µg per mouse).

a) Immunization of Mice

BALB/c mice were each immunized intraperitoneally with 20 µg of immunizing antigen (prothrombin) in complete Freund's adjuvant. A booster took place with in each case 20 μg of immunizing antigen in incomplete Freund's adjuvant (from ICN Biomedical GmbH, Eschwege, Germany) after 4 weeks and with in each case 20 μg of immunizing antigen without Freund's adjuvant after 8 weeks. For the last 3 days before the fusion, the mice received intravenous boosters with in each case 20 μg of immunizing antigen.

b) Fusion

After the mice had been sacrificed by inhalation of $CO_2$, the spleens were removed and single-cell suspensions were prepared in serum-free Dulbeccos modified Eagle medium (DMEM, from CC Pro GmbH, Neustadt/W, Germany). The cells were centrifuged (652 g) and washed 2× in DMEM. The cell count was then determined by Trypan blue staining. $2\times10^7$ myeloma cells (Sp2/0) were added to about $10^8$ spleen cells. After centrifugation (360 g), the supernatant was discarded, 1 ml of polyethylene glycol solution (PEG 4000, from Merck Eurolab, Bruchsal, Germany; approx. 50% strength in DMEM) was added to the cell pellet and incubated after resuspension at 37° C. for 1 minute. Then approx. 10 ml of DMEM were added dropwise, and the mixture was incubated at room temperature for 2 to 4 minutes. The fused cells were centrifuged (326 g) and the pellet was resuspended in DMEM+20% FCS (fetal calf serum, from Bio Whittaker Europe, Verviers, Belgium)+HAT solution (CC Pro GmbH, Neustadt/W, Germany) and dispensed into 24-well cell culture plates (from Costar). The approximate cell concentration per well was $5\times10^4$ to $5\times10^6$ cells.

2-3 weeks later, the resulting cell colonies (hybrids) were removed and transferred into new culture plates.

c) Screening

The specificity of the antibodies released into the cell culture was tested in a first test step with the aid of prothrombin-coated microtiter plates (from Nunc, type B), coating 1 μg/ml≈0.15 μg/well.

100 μl of cell culture supernatant (dilution 1:2) were pipetted into each well of the microtiter plate and incubated at +15 to +25° C. for 1 hour. After the plate had been washed twice with POD washing solution (OSEW; from Dade Behring, Marburg, Germany), 100 μl of anti-mouse IgG/F(ab')$_2$—POD conjugate (from Dade Behring, Marburg, Germany) were introduced into each well and incubated at +15 to +25° C. for 1 hour. After the plate had again been washed twice, 100 μl of chromogen TMB solution (from Dade Behring, Marburg, Germany) were introduced into each well and incubated at +15 to +25° C. for a further 30 minutes. After the incubation, 100 μl of POD stock solution (from Dade Behring, Marburg, Germany) were introduced into each well, and the microtiter plate was evaluated in a BEP II (Behring ELISA processor II, from Dade Behring, Marburg, Germany) at 450 nm.

In a 2nd test step, the hybrids after isolation were checked once again in the same test format as described above.

d) Cloning

Single cells of hybrids which produce prothrombin-specific antibodies were cloned using a micromanipulator (from Leitz, Wetzlar, Germany). Culture supernatants from these clones were purified as described under g) and characterized in detail as described under e), h) and i). An antibody of the invention (binding to an epitope in the N-terminal half/region of the human prothrombin fragment F2) is produced for example by the clone 92-195/097. This hybridoma cell line was deposited at the DSMZ Deutsche Sammlung von Mikroorganismen and Zellkulturen GmbH, Mascheroder Weg 1b, 38124 Brunswick, Germany, with the accession number DSM ACC2607.

e) Antibody Subclass Determination

The subclass of the antibody 92-195/097 was determined using the IsoStrip™ mouse monoclonal antibody isotyping kit from Boehringer Mannheim, Germany, to be $IgG_1$.

f) Antibody Production

Larger amounts of antibodies are produced by transferring the appropriate cell clones into roller bottles (from Corning Costar Deutschland, Bodenheim) and expanding to the desired final volume at +37° C. The roller culture suspension is then filtered through 0.22 μm to remove the cells. The antibody solution, which is now cell-free, is concentrated by ultra-filtration (separation limit 30 000 dalton) and then purified.

g) Antibody Purification

The resulting antibody solution buffer is changed to 0.14 M phosphate buffer pH 8.6 and the solution is loaded onto a chromatography column packed with rProtein A Sepharose Fast Flow (from Amersham Pharmacia) (1 ml of rProtein A Sepharose Fast Flow is employed per 10 mg of antibodies to be purified). All unbound components are removed by washing the column with 0.14 M phosphate buffer pH 8.6. The bound antibody is eluted from the column with 0.1 M citric acid pH 3.0 and dialyzed against 0.05 M sodium acetate+0.5 M NaCl+0.05 M tris+0.01% sodium azide pH 7.0.

h) Selection of Suitable Antibodies for a Prothrombin Fragment $F_{1+2}$ Sandwich ELISA Reaction of the monoclonal anti-prothrombin antibodies with thrombin and with $F_2$ was investigated:

Reaction with Thrombin:

The solid phase used is a microtiter plate coated with rabbit anti-mouse IgG. Anti-prothrombin antibodies from culture supernatants are coupled thereto. A washing step is followed by incubation with purified thrombin. After a further washing step, the binding of the antibody to thrombin is detected through a conjugate consisting of monoclonal mouse anti-thrombin antibodies and the enzyme peroxidase with subsequent color reaction.

Reaction with $F_2$:

The solid phase used is a microtiter plate coated with rabbit anti-mouse IgG. Anti-prothrombin antibodies from culture supernatants are coupled thereto. A washing step is followed by incubation with purified prothrombin fragment $F_2$. After a further washing step, the binding of the antibody to $F_2$ is detected through a conjugate consisting of polyclonal rabbit anti-$F_2$ antibodies and the enzyme peroxidase with subsequent color reaction.

The antibodies selected were those which showed a reaction with $F_2$ but at the same time did not react with thrombin. The suitability of these antibodies for use as conjugate in a sandwich ELISA with $F_2$- and $F_{1+2}$-specific primary antibodies was investigated. For this purpose, the purified antibodies were coupled to horseradish peroxidase by a method known to the skilled worker (Nakane coupling).

The suitability was checked in a sandwich ELISA as described in example 3a). The essential criteria for deciding about suitability were an optimal signal strength, size of the measurement range, lower limit of detection, and the linearity of the calibration plot.

The antibody produced by the clone 92-195/097 showed the best results in relation to these criteria.

i) Epitope Mapping

Prothrombin fragment $F_{1+2}$ was divided into 13-mer peptides each of which overlap by 11 amino acids and accordingly progress in 2-mer steps successively from the N terminus to the C terminus. These peptides were prepared by synthesis and coupled to a membrane, and the binding of the antibody to be analyzed to each of these peptides was investigated: for detection, the antibody to be investigated had previously been covalently coupled to horseradish peroxidase. In a subsequent reaction, the horseradish peroxidase converts a chemiluminescent substrate whose signal is quantified using an imaging system. This means that a stronger measured signal is obtained with a particular peptide when more antibody has bound to this peptide.

The reason for the low yield in the search for a suitable secondary antibody is evidently that a specific binding site of the secondary antibody preferably in the N-terminal half of the $F_2$ fragment is necessary for combination with a primary antibody against the free C terminus of the prothrombin $F_{1+2}$ fragment. In particular, specific binding to the amino acid sequence Ser-Pro-Pro-Leu-Glu-Gln-Cys (amino acids 9 to 15 of SEQ ID NO:2) is preferred.

Epitope mapping of the secondary antibody produced by the clone 92-195/097, result (an extract from a total of 180 peptides whose amino acid sequence is displaced in each case by 2 amino acids per peptide is shown):

| Peptide | Sequence | Signal strength |
|---|---|---|
| 100 | Ser-Glu-Gly-Ser-Ser-Val-Asn-Leu-Ser-Pro-Pro-Leu-Glu<br>Amino acids 1 to 13 of SEQ ID NO: 2 | 12842 |
| 101 | Gly-Ser-Ser-Val-Asn-Leu-Ser-Pro-Pro-Leu-Glu-Gln-Ser*<br>SEQ ID NO: 3 | 350189 |
| 102 | Ser-Val-Asn-Leu-Ser-Pro-Pro-Leu-Glu-Gln-Ser*-Val-Pro<br>SEQ ID NO: 4 | 406370 |
| 103 | Asn-Leu-Ser-Pro-Pro-Leu-Glu-Gln-Ser*-Val-Pro-Asp-Arg<br>SEQ ID NO: 5 | 434256 |
| 104 | Ser-Pro-Pro-Leu-Glu-Gln-Ser*-Val-Pro-Asp-Arg-Gly-Gln<br>SEQ ID NO: 6 | 538562 |
| 105 | Pro-Leu-Glu-Gln-Ser*-Val-Pro-Asp-Arg-Gly-Gln-Gln-Tyr<br>SEQ ID NO: 7 | 102606 |
| 106 | Glu-Gln-Ser*-Val-Pro-Asp-Arg-Gly-Gln-Gln-Tyr-Gln-Gly<br>SEQ ID NO: 8 | 15952 |
| 107 | Ser*-Val-Pro-Asp-Arg-Gly-Gln-Gln-Tyr-Gln-Gly-Arg-Leu<br>SEQ ID NO: 9 | 14287 |
| 108 | Pro-Asp-Arg-Gly-Gln-Gln-Tyr-Gln-Gly-Arg-Leu-Ala-Val<br>Amino acids 17 to 29 of SEQ ID NO: 2 | 13364 |
| 109 | Arg-Gly-Gln-Gln-Tyr-Gln-Gly-Arg-Leu-Ala-Val-Thr-Thr<br>Amino acids 19 to 31 of SEQ ID NO: 2 | 13017 |

*For technical reasons, cysteine in the original sequence was replaced by serine for the peptide synthesis. The immunoreactivity of the antibody for the two amino acids does not differ in this method. The exchange therefore has no influence on the final result.

Example 3

Detection of $F_{1+2}$ in a Sample a) Assay Method

The secondary antibodies of the invention were employed in combination with the primary antibodies in an enzyme immunoassay according to the sandwich principle:

During the first incubation, the $F_{1+2}$ antigen present in the sample binds to the primary antibodies which are directed against $F_{1+2}$ and are immobilized on the surface of wells of a microtiter plate. After the wells have been washed, peroxidase-conjugated secondary antibodies of the invention are bound to the free $F_{1+2}$ determinants in a second reaction. The excess enzyme-conjugated secondary antibodies are washed out. The bound enzymic activity in the wells is then determined. The enzymatic conversion of hydrogen peroxide and tetramethylbenzidine is stopped by adding dilute sulfuric acid. The color intensity, which is proportional to the $F_{1+2}$ concentration, is determined by photometry and quantified by means of a calibration plot derived from the standards also supplied.

Such a sandwich immunoassay of the invention shows results which are improved compared with known $F_{1+2}$ assays in respect of the following properties:

b) Assay Homogeneity:

The homogeneity of a sample measured on 20 assay plates with in each case 96 determinations amounts to a CV (=coefficient of variation) of 5.2%.

c) Linearity of the Measurement Range:

There is linear dilutability over the entire measurement range:

| Sample A | nmol/l | nmol/l × dilution | % recovery |
|---|---|---|---|
| Undil. | 3.940 | 3.94 | 100% |
| 1:2 | 2.060 | 4.12 | 105% |
| 1:4 | 0.985 | 3.94 | 100% |
| 1:16 | 0.206 | 3.30 | 84% |

| Sample B | nmol/l | nmol/l × dilution | nmol/l × dilution |
|---|---|---|---|
| Undil. | 0.900 | 0.90 | 100% |
| 1:2 | 0.430 | 0.86 | 96% |
| 1:5 | 0.166 | 0.83 | 92% |
| 1:8 | 0.114 | 0.91 | 101% |
| 1:10 | 0.081 | 0.81 | 90% |
| 1:15 | 0.064 | 0.96 | 107% | d) Diagnostic Sensitivity:

The diagnostic sensitivity of the sandwich immunoassay of the invention is improved compared with the prior art:

| Diagnostic sensitivity* | With monoclonal antibodies | Prior art (commercially available assay) |
|---|---|---|
| In orally anticoagulated patients (n = 18): | 83% | 78% |
| In thrombophilia patients (n = 18): | 67% | 61% |

(*with 95% diagnostic specificity; n = 40)

The invention claimed is:

1. An isolated peptide consisting of amino acids 9 to 15 of SEQ ID NO: 2.

2. An isolated peptide consisting of amino acids 1 to 25 of SEQ ID NO: 2.

3. The isolated peptide as claimed in claim 1, wherein the peptide is associated with at least one of a solid phase and a component of a signal-generating system.

4. A reagent comprising the peptide as claimed in claim 1.

5. A test kit comprising the reagent as claimed in claim 4.

6. The isolated peptide as claimed in claim 2, wherein the peptide is associated with at least one of a solid phase and a component of a signal-generating system.

7. A reagent comprising the peptide as claimed in claim 2.

8. A test kit comprising the reagent as claimed in claim 7.

9. A method of immunization comprising administering the peptide as claimed in claim 1 to a non-human animal and allowing said peptide to produce an immune response.

10. A method of purifying or isolating an antibody that binds specifically to the peptide of claim 1, comprising contacting a sample containing the antibody with the peptide as claimed in claim 1, allowing said antibody to bind to said peptide, and removing unbound substances contained in said sample.

11. A method for the quantitative or qualitative detection of an analyte, wherein the analyte is prothrombin fragment $F_{1+2}$ and/or $F_2$, comprising contacting a sample containing the analyte with the peptide as claimed in claim 1 and with an analyte-specific antibody, allowing said analyte to associate with the antibody, wherein the peptide competes with the analyte for binding to the antibody, and determining the amount, concentration, or presence of said analyte in the sample by measuring the competing peptide bound to the antibody via a label associated with the peptide.

12. A method for the quantitative or qualitative detection of at least one sample analyte chosen from prothrombin fragments $F_{1+2}$ and $F_2$ in a sample comprising performing a competitive binding assay comprising (a) contacting the sample with an analyte-specific antibody and a reagent analyte, a component of a signal-generating system being associated, directly or indirectly, with the analyte-specific antibody or the reagent analyte, and (b) detecting binding, quantitatively or qualitatively, of the reagent analyte to the analyte-specific antibody by detecting signal from the signal-generating system, wherein the analyte-specific antibody comprises at least one monoclonal antibody which binds specifically to a peptide comprising an epitope having the amino acid sequence Ser-Pro-Pro-Leu-Glu-Gln-Cys (amino acids 9-15 of SEQ ID NO:2), wherein the monoclonal antibody specifically binds said sequence, and wherein the reagent analyte comprises at least one peptide as claimed in claim 1.

13. A method for the quantitative or qualitative detection of at least one sample analyte chosen from prothrombin fragments $F_{1+2}$ and $F_2$ in a sample comprising performing a competitive binding assay comprising (a) contacting the sample with an analyte-specific antibody and a reagent analyte, and (b) detecting binding, quantitatively or qualitatively, of the reagent analyte to the analyte-specific antibody, wherein the analyte-specific antibody comprises at least one monoclonal antibody which binds specifically to a peptide comprising an epitope having the amino acid sequence Ser-Pro-Pro-Leu-Glu-Gln-Cys (amino acids 9-15 of SEQ ID NO:2), wherein the reagent analyte comprises at least one peptide as claimed in claim 1, and wherein (i) the reagent analyte is directly or indirectly associated with a component of a signal-generating system and the analyte-specific antibody is directly or indirectly solid-phase associated, or (ii) the analyte-specific antibody is directly or indirectly associated with a component of a signal-generating system and the reagent analyte is directly or indirectly solid-phase associated.

14. A method for the quantitative or qualitative detection of at least one sample analyte chosen from prothrombin fragments $F_{1+2}$ and $F_2$ in a sample comprising performing a competitive binding assay comprising (a) contacting the sample with an analyte-specific antibody and a reagent analyte, (b) allowing the reagent analyte and the sample analyte to compete for binding to said analyte-specific antibody, wherein binding of analyte-specific antibody to reagent analyte results in solid-phase association of a component of a signal-generating system directly or indirectly associated with the analyte-specific antibody or the reagent analyte; and (c) detecting or measuring signal from the signal-generating system qualitatively or quantitatively, wherein the analyte-specific antibody comprises at least one monoclonal antibody which binds specifically to a peptide comprising an epitope having the amino acid sequence Ser-Pro-Pro-Leu-Glu-Gln-Cys (amino acids 9-15 of SEQ ID NO:2), and wherein the reagent analyte comprises at least one peptide as claimed in claim 1.

15. A method of immunization comprising administering the peptide as claimed in claim 2 to a non-human animal and allowing said peptide to produce an immune response.

16. A method of purifying or isolating an antibody that binds specifically to the peptide of claim 2, comprising contacting a sample containing the antibody with the peptide as claimed in claim 2, allowing said antibody to bind to said peptide, and removing unbound substances contained in said sample.

17. A method for the quantitative or qualitative detection of an analyte, wherein the analyte is prothrombin fragment $F_{1+2}$ and/or $F_2$, comprising contacting a sample containing the analyte with the peptide as claimed in claim 2 and with an analyte-specific antibody, allowing said analyte to associate with the antibody, wherein the peptide competes with the analyte for binding to the antibody, and determining the amount, concentration, or presence of said analyte in the sample by measuring the competing peptide bound to the antibody via a label associated with the peptide.

18. A method for the quantitative or qualitative detection of at least one sample analyte chosen from prothrombin fragments $F_{1+2}$ and $F_2$ in a sample comprising performing a competitive binding assay comprising (a) contacting the sample with an analyte-specific antibody and a reagent analyte, a component of a signal-generating system being associated, directly or indirectly, with the analyte-specific antibody or the reagent analyte, and (b) detecting binding, quantitatively or qualitatively, of the reagent analyte to the analyte-specific antibody by detecting signal from the signal-generating system, wherein the analyte-specific antibody comprises at least one monoclonal antibody which binds specifically to a peptide comprising an epitope having the amino acid sequence Ser-Pro-Pro-Leu-Glu-Gln-Cys (amino acids 9-15 of SEQ ID NO:2), wherein the monoclonal antibody specifically binds said sequence, and wherein the reagent analyte comprises at least one peptide as claimed in claim 2.

19. A method for the quantitative or qualitative detection of at least one sample analyte chosen from prothrombin fragments $F_{1+2}$ and $F_2$ in a sample comprising performing a competitive binding assay comprising (a) contacting the sample with an analyte-specific antibody and a reagent analyte, and (b) detecting binding, quantitatively or qualitatively, of the reagent analyte to the analyte-specific antibody, wherein the analyte-specific antibody comprises at least one monoclonal antibody which binds specifically to a peptide comprising an epitope having the amino acid sequence Ser-Pro-Pro-Leu-Glu-Gln-Cys (amino acids 9-15 of SEQ ID NO:2), wherein the reagent analyte comprises at least one peptide as claimed in claim 2, and wherein (i) the reagent analyte is directly or indirectly associated with a component of a signal-generating system and the analyte-specific antibody is directly or indirectly solid-phase associated, or (ii) the analyte-specific antibody is directly or indirectly associated with a component of a signal-generating system and the reagent analyte is directly or indirectly solid-phase associated.

20. A method for the quantitative or qualitative detection of at least one sample analyte chosen from prothrombin fragments $F_{1+2}$ and $F_2$ in a sample comprising performing a competitive binding assay comprising (a) contacting the sample with an analyte-specific antibody and a reagent analyte, (b) allowing the reagent analyte and the sample analyte to compete for binding to said analyte-specific antibody, wherein binding of analyte-specific antibody to reagent analyte results in solid-phase association of a component of a signal-generating system directly or indirectly associated with the analyte-specific antibody or the reagent analyte; and (c) detecting or measuring signal from the signal-generating system qualitatively or quantitatively, wherein the analyte-specific antibody comprises at least one monoclonal antibody which binds specifically to a peptide comprising an epitope having the amino acid sequence Ser-Pro-Pro-Leu-Glu-Gln-Cys (amino acids 9-15 of SEQ ID NO:2), and wherein the reagent analyte comprises at least one peptide as claimed in claim 2.

* * * * *

UNITED STATES PATENT AND TRADEMARK OFFICE
CERTIFICATE OF CORRECTION

PATENT NO. : 8,063,180 B2  
APPLICATION NO. : 12/591303  
DATED : November 22, 2011  
INVENTOR(S) : Teigelkamp et al.

It is certified that error appears in the above-identified patent and that said Letters Patent is hereby corrected as shown below:

Title page, item (73), Assignee, "Seimens Healthcare Diagnostics Products GmbH" should read -- Siemens Healthcare Diagnostics Products GmbH --.

Signed and Sealed this  
Fifteenth Day of May, 2012

David J. Kappos  
*Director of the United States Patent and Trademark Office*

SEQUENCE LISTING

<160> NUMBER OF SEQ ID NOS: 9

<210> SEQ ID NO 1
<211> LENGTH: 4
<212> TYPE: PRT
<213> ORGANISM: Homo sapiens

<400> SEQUENCE: 1

Ile Glu Gly Arg
1

<210> SEQ ID NO 2
<211> LENGTH: 62
<212> TYPE: PRT
<213> ORGANISM: Homo sapiens

<400> SEQUENCE: 2

Ser Glu Gly Ser Ser Val Asn Leu Ser Pro Pro Leu Glu Gln Cys Val
1               5                   10                  15

Pro Asp Arg Gly Gln Gln Tyr Gln Gly Arg Leu Ala Val Thr Thr His
            20                  25                  30

Gly Leu Pro Cys Leu Ala Trp Ala Ser Ala Gln Ala Lys Ala Leu Ser
        35                  40                  45

Lys His Gln Asp Phe Asn Ser Ala Val Gln Leu Val Glu Asn
    50                  55                  60

<210> SEQ ID NO 3
<211> LENGTH: 13
<212> TYPE: PRT
<213> ORGANISM: Homo sapiens

<400> SEQUENCE: 3

Gly Ser Ser Val Asn Leu Ser Pro Pro Leu Glu Gln Ser
1               5                   10

<210> SEQ ID NO 4
<211> LENGTH: 13
<212> TYPE: PRT
<213> ORGANISM: Homo sapiens

<400> SEQUENCE: 4

Ser Val Asn Leu Ser Pro Pro Leu Glu Gln Ser Val Pro
1               5                   10

<210> SEQ ID NO 5
<211> LENGTH: 13
<212> TYPE: PRT
<213> ORGANISM: Homo sapiens

<400> SEQUENCE: 5

Asn Leu Ser Pro Pro Leu Glu Gln Ser Val Pro Asp Arg
1               5                   10

<210> SEQ ID NO 6
<211> LENGTH: 13
<212> TYPE: PRT
<213> ORGANISM: Homo sapiens

<400> SEQUENCE: 6

Ser Pro Pro Leu Glu Gln Ser Val Pro Asp Arg Gly Gln
1               5                   10

```
<210> SEQ ID NO 7
<211> LENGTH: 13
<212> TYPE: PRT
<213> ORGANISM: Homo sapiens

<400> SEQUENCE: 7

Pro Leu Glu Gln Ser Val Pro Asp Arg Gly Gln Gln Tyr
1               5                   10

<210> SEQ ID NO 8
<211> LENGTH: 13
<212> TYPE: PRT
<213> ORGANISM: Homo sapiens

<400> SEQUENCE: 8

Glu Gln Ser Val Pro Asp Arg Gly Gln Gln Tyr Gln Gly
1               5                   10

<210> SEQ ID NO 9
<211> LENGTH: 13
<212> TYPE: PRT
<213> ORGANISM: Homo sapiens

<400> SEQUENCE: 9

Ser Val Pro Asp Arg Gly Gln Gln Tyr Gln Gly Arg Leu
1               5                   10
```